April 16, 1963 C. FISCHER Plant Pat. 2,252
GLADIOLUS PLANT
Filed May 9, 1962
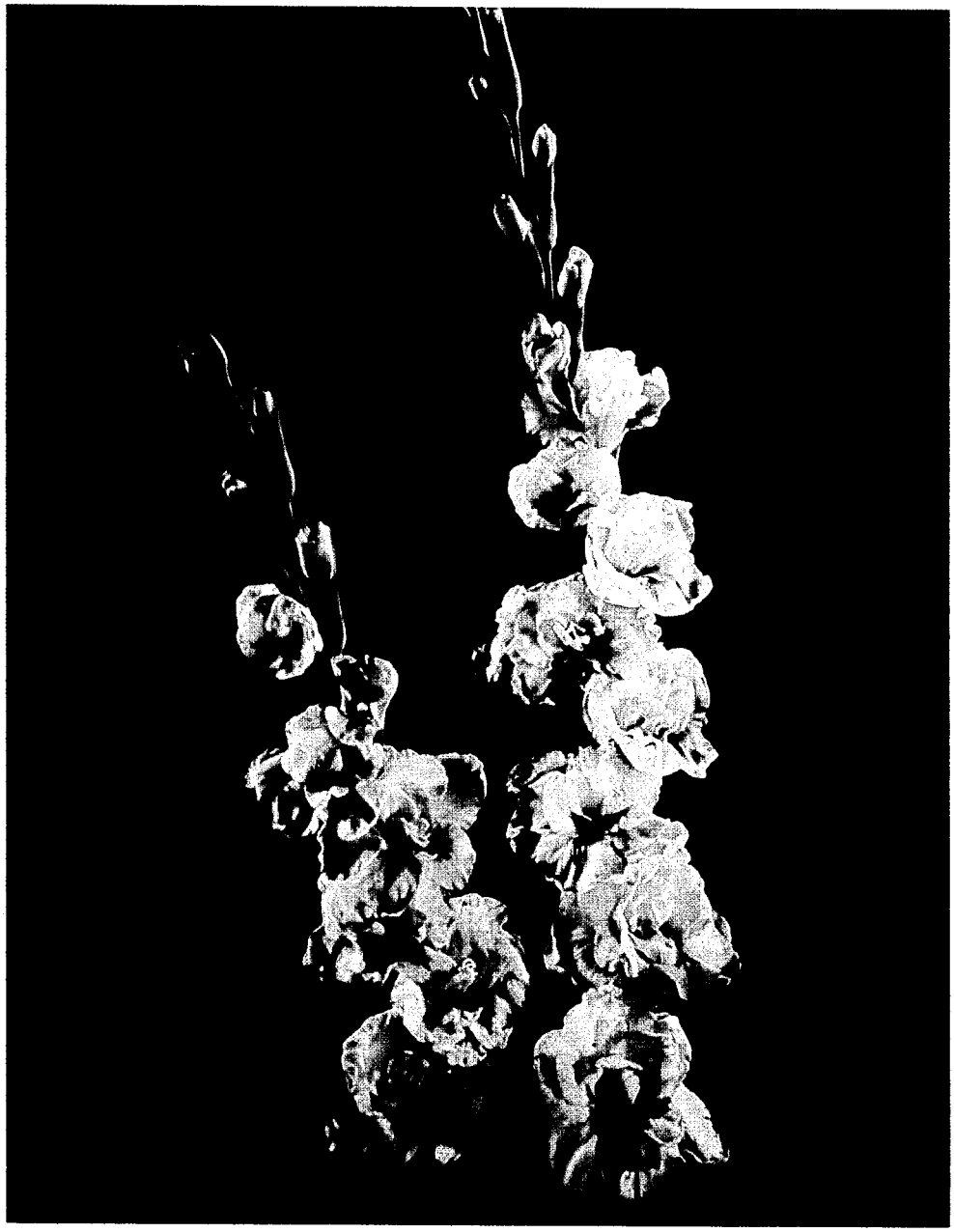
Inventor.
Carl Fischer
By: Robb & Robb
Attorneys.

United States Patent Office

Plant Pat. 2,252
Patented Apr. 16, 1963

2,252
GLADIOLUS PLANT

Carl Fischer, St. Charles, Minn., assignor to Imperial Flowers Limited, Leamington, Ontario, Canada, a corporation of Ontario Filed May 9, 1962, Ser. No. 193,638
1 Claim. (Cl. 47—60)

The present invention relates to a new and distinct variety of gladiolus plant which was originated by me by crossing two unnamed and unpatented varieties of unknown parentage.

As the result of this breeding, which was performed by manual cross pollination in my outdoor breeding fields at St. Charles, Minnesota, I have produced a new variety of gladiolus plant which is distinguished from its parents, as well as from all other varieties of which I am aware, and which is particularly characterized as to novelty by the consistently double form of each floret of the flower heads, combined with an attractive and distinctive yellow general color tonality of the flowers, said yellow color being blotched and edged with shades of red which present a striking and unusually attractive appearance.

My new variety does not resemble any other existing variety known to me, and I believe it is the only variety in which all florets of the flower heads are consistently double in form.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows typical specimen flower spikes of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Moderately vigorous; slow propagator; flower spike attains height averaging between 30 inches and 34 inches.

Blooming habit: Mid-season bloomer in the northern latitudes of the United States; comes into bloom from large bulbs in about 85 days.

Stems: Straight; slender. Diameter at base—¼ inch.

Foliage: Low growing (from 14 inches to 16 inches tall); leaves range from 1 inch to 1¼ inches wide. Color—deep green.

Disease resistance: Unusually resistant to Fusarium yellows, Sclerotina dry rot and Septoria leaf spot, as determined by comparison with other varieties grown in my fields near St. Charles, Minnesota, in irrigated black loam soil.

Corms (bulbs): Normal; healthy; straw-colored husks cover the corms well. Color of flesh—Empire Yellow, Plate 603/2.

*Flower*

Spike: Well proportioned in relation to plant; bears from 14 to 16 buds with 6 usually opening at once and with 5 or 6 buds showing color.

Bud:

*Size.*—From 1½ inches to 1¾ inches long when opening.

*Opening.*—5 or 6 buds show color at one time; opens well.

Flower:

*Arrangement.*—Florets are informally arranged on stem and usually all face forward.

*Size.*—Individual florets range from 2½ inches to 3 inches in diameter, with upper blooms being progressively smaller.

*Form.*—Florets are round, ruffled and open flat, with the extreme edges of the petals rolled forward.

*Keeping qualities.*—Keeps well.

Petals:

*Shape.* — Outer petals — broad and ruffled. Inner petals—smaller in size than outer petals, with some creasing which gives effect of doubling.

*Size.* — Outer petals — 1¼ inches wide. Inner petals—from ½ inch to 1 inch wide.

*Aspect.*—Average substance.

*Fragrance.*—None.

*Color.*—Amber Yellow, Plate 505/2, shading to Amber Yellow, Plate 505/1 at deepest color, with throat blotch ranging between Current Red, Plate 821 and Currant Red, Plate 821/3, and with tints of latter color at the edge of the blotch and on the petal tips; buds are tinted with Currant Red, Plate 821 at the tips before they begin to unfold and similar color suffusion also shows on the reverse of the petals.

*Reproductive Organs*

Stamens: None; petals form where stamens usually develop.

Pistil: Color—light buff.

I claim:

A new and distinct variety of gladiolus plant, substantially as herein shown and described, characterized particularly as to novelty by the unique combination of a consistently double form of each floret of the flower heads, and a distinctive and attractive yellow general color tonality of the flowers, with red throat blotches and with red shadings on the petal tips.

No references cited.